(12) United States Patent
Roberts et al.

(10) Patent No.: US 7,972,610 B2
(45) Date of Patent: Jul. 5, 2011

(54) ANTIMICROBIAL COMPOUNDS

(75) Inventors: Craig William Roberts, Glasgow (GB); Fiona Roberts, Glasgow (GB); Fiona Luisa Henriquez, Glasgow (GB); Paul Richard Ingram, Glasgow (GB)

(73) Assignee: University of Strathclyde, Glasgow (GB)

( * ) Notice: Subject to any disclaimer, the term of this patent is extended or adjusted under 35 U.S.C. 154(b) by 0 days.

(21) Appl. No.: 11/908,377

(22) PCT Filed: Mar. 13, 2006

(86) PCT No.: PCT/GB2006/000875
§ 371 (c)(1),
(2), (4) Date: Feb. 29, 2008

(87) PCT Pub. No.: WO2006/095195
PCT Pub. Date: Sep. 14, 2006

(65) Prior Publication Data
US 2008/0249051 A1    Oct. 9, 2008

(30) Foreign Application Priority Data

Mar. 11, 2005  (GB) .................................. 0504998.6

(51) Int. Cl.
*A61K 39/002*    (2006.01)
(52) U.S. Cl. .................................. 424/269.1; 424/234.1
(58) Field of Classification Search .......................... None
See application file for complete search history.

(56) References Cited

FOREIGN PATENT DOCUMENTS
WO    WO 02/083629    10/2002
WO    WO 2004/069998    8/2004

OTHER PUBLICATIONS

David P. Casemore, Sensitivity of hartmannella (*Acanthamoeba*) to 5-fluorocytosine, hydroxystilamidine, and other substances, 1970, Journal of Clinical Pathology, vol. 23, pp. 649-652.*
Roberts et al., "Evidence for the shikimate pathway in apicomplexan parasites," *Nature*, Jun. 1998, pp. 810-805, vol. 393, No. 6687.
Roberts et al., "The shikimate pathway and its branches in apicomplexan parasites," *Journal of Infectious Diseases*, Feb. 2002, pp. 25-36, vol. 185.
Elandalloussi et al., "Shikimate and folate pathways in the protozoan parasite, *Perkinsus olseni*," *Molecular and Biochemical Parasitology*, Jul. 2005, pp. 106-109, vol. 142, No. 1.
McConkey, G., "Targeting the shikimate pathway in the malaria parasite *Plasmodium falciparum*," *Antimicrobial Agents and Chemotherapy*, Jan. 1999, pp. 175-177, vol. 43, No. 1.
McRobert et al., "*Plasmodium falciparum*: Interaction of shikimate analogues with antimalarial drugs," *Experimental Parasitology*, Nov. 2005, pp. 178-181, vol. 111, No. 3.
McRobert et al., "RNA interference (RNAi) inhibits growth of *Plasmodium falciparum*," *Molecular and Biochemical Parasitology*, Feb. 2002, pp. 273-278, vol. 119, No. 2.
Peterson et al., "New simplified inhibitors of EPSP synthase: the importance of ring size for recognition at the Shikimate 3-phosphate site," *Bioorganic & Medicinal Chemistry Letters*, Dec. 3, 1996, pp. 2853-2858, vol. 6, No. 23.
Schuster, et al., "Free-living amoebae as opportunistic and non-opportunistic pathogens of humans and animals," *International Journal of Parasitology*, Aug. 2004, pp. 1001-1027, vol. 39, No. 9.
International Search Report, dated Aug. 16, 2006.

* cited by examiner

*Primary Examiner* — Jennifer E Graser
(74) *Attorney, Agent, or Firm* — Alston & Bird LLP (57) ABSTRACT

The present invention relates to compounds that modulate the shikimate pathway and/or a pathway branching from the shikimate pathway in members of the Amoebida Order. In particular these compounds may be useful in the treatment or prevention of diseases caused or contributed to by members of the Amoebida Order.

2 Claims, 6 Drawing Sheets

ATGCAGAAGAAGGGAGGGGATTTCGTTGTGGAGGATGTGCCGGTGGAGCGGGTGGAG
GGAGGCAAGGAGCCGATCGTTATCGGCAACGAGATCCTGCGCAAGGGCTGGATCGCG
CGCGACATCCGCGAGCGAGTGCCCAAGGCGGTGAAGTTCGTCATCGTCACCGACTCG
AACGTGTTCGGGCTCTACGGTCAGACCTTCATCTCGACCTTCGAGCAGGTGCTCCAC
ATCAAGCCCTTTGTCAAAGTGCTGCCACCGGGCGAGGAGACCAAGAGCCGGCAGGTC
AAGGAGGAGATCGAAGATTTCATGCTCGCCAAGGCTTGCAATCGCGACACCTGCGTG
GTCGCCCTGGGTGGTGGTGTCATTGGCGATCTCGCTGGATTCGTGGCTGCCACCTAC
CTCCGAGGGGTGCCTTTCGTGCAAGTACCAACCACCCTCCTGGCCATGGTGGACTCT
TCGATCGGCGGCAAGACTGGACTCAACCCGCCAGCGGGCAAGAACCTCGTGGGCGCG
TTCCACCACCCCAAGGCAGTCTACATCGATCTGTCGCTCCTCAAAACTCTTCCCCAG
CGCGAGTTCTGTAACGGCCTTGCCGAGGTCATCAAGTCTGGAGTGATCAGGGACCCC
GAGCTGTTCGAATTGCTGGAGACCAACGTGGACGGCATCCTCAACAACAGGGAGGAG
CGTTTGCTTCGGGAGATCGTGCACCGATCGGCCAAGATGAAGGCCGAGGTGGTCATG
ATGGACGCCAACGAAAACGGCATCCGTTGCATCCTCAACTACGGACACACGATCGGC
CATGCCATCGAGGCCTTTGCCTTCCCGCTCCTTCTGCACGGAGAGTGCGTGTCGATT
GGCATGGTACGCGCACGACACACAACGCACACGCACGCACACGCGTCATTTCAGTTA
ACACATCGGTTTTTCAATGTGGCACGGCGGTACCAGGTGCTCGAGAGCAAGCTGGCA
CAGAAGATGAACCACCTCAAGAACCTCAACTTCATTGGCCGGCTGACGCGATGCCTG
CAGGCCTACAAGCTCGAAGACCTGATCAACAAGATGCTCATCGACAAGAAGAACGCC
AACAGCAACATCCGATGCGTGATCGTCAAGGACTTCGGCGATGTGTTCGAACACCCC
GTCGTTGTTGACAAGGACACGCTCAGGTTTGTGCTTTTGCCCTCCGTGGCGGTGGAG
CCCACCCAGAGCGGCGTGAGCGGCGTGATCACCGTGCCCGGCTCCAAGTCGATCTCC
AACCGCGTGTTGACTCTTGCCGCCCTGGGCGAAGGAGGCGAATGTCACATCAAGGGG
CTTCTCTCGGCCGACGACACGGGCGTGATGCTCGCCGCGCTTCGACGACTCGGTGTC
CAGTACAAGTGGCTCGACCAAGGCCTCGTAAGCGCCTCCCCCCTGCATCTGTCTGCC
GACAACAGCTCACCCCAGTCACCACCC

Figure 3

MQKKGGDFVVEDVPVERVEGGKEPIVIGNEILRKGWIARDIRERVPKAVKFVIVTDS
NVFGLYGQTFISTFEQVLHIKPFVKVLPPGEETKSRQVKEEIEDFMLAKACNRDTCV
VALGGGVIGDLAGFVAATYLRGVPFVQVPTTLLAMVDSSIGGKTGLNPPAGKNLVGA
FHHPKAVYIDLSLLKTLPQREFCNGLAEVIKSGVIRDPELFELLETNVDGILNNREE
RLLREIVHRSAKMKAEVVMMDANENGIRCILNYGHTIGHAIEAFAFPLLLHGECVSI
GMVRARHTTHTHAHASFQLTHRFFNVARRYQVLESKLAQKMNHLKNLNFIGRLTRCL
QAYKLEDLINKMLIDKKNANSNIRCVIVKDFGDVFEHPVVVDKDTLRFVLLPSVAVE
PTQSGVSGVITVPGSKSISNRVLTLAALGEGGECHIKGLLSADDTGVMLAALRRLGV
QYKWLDQGLVSASPLHLSADNSSPQSPP

Figure 4

ATGAGCAGCTTTGGCAGAGCGTTTCGAGTGACCACCTTCGGTGAATCGCACGGCGGC
GGAGTGGGATGCATTATCTCCTTTGCAGATGGAGTGCCGCCCTGCCTGCCCCTCACC
GAAGCCGACATCCAGCCGCAGCTCAGCCGTCGCCGCCCCGGCCAGAGCTCCCTCACC
ACCCCCGTGTCTCATCAGAGGAATGAGGCGGACCAGGTGAAGATCCAGGCCGGCACG
GAGAACGGGTACACGCTGGGCTCGCCGATCAGCCTCTTCGTGGCCAACCAGGACCAG
CGGCCCGTCGACTACTCGGACATGTCCAAGATTGAGGCGGCAAAGGCTGACAAGGAC
AGCATCGGCGGCGTGGTGACGTGCGTGTGCCGTAACGTACCGACGGGCCTGGGCGAG
CCCTGCTTCGACAAGCTCGAGGCCATGCTCGCCCACGCCATGCTCTCCATCCCGGCC
ACGAAGGGGTTCGAGATCGGCAGCGGCTTCGCGGGCACGCGGATGCGGGGCAGCAAG
CACAACGACCCCTTCGTGGTCAAGACCGGGGCCGACGGCAAGAAGCGGCTCGGTACC
ACTACCAACCACAGCGGCGGCATCCAGGGCGGAATCACCAACGGCGAACACGTCGTC
TTCAAGGTGGCGTTCAAGCCGCCGGCCACGATTAGCCAGGCGCAGAAGACG

Figure 5

GAGTTCTTGGACACCATCAGCCCGCAGTTCGTGGCCGACCTGGTCTCCTGGGGCGCC
ATCGGAGCGCGCACCACCGAGAGCCAGGTGCACCGCGAGCTGGCCTCCGGTCTGTCC
GTCCCTGTCGGTTTCAAGAATGGTAGGCGCCCTGCCTTGCCTGTGCGATTGTGTGGC
GTGTGCGTGTGCGGTGGTGCTAACAAGATGGTACCCGAGCCAGGCACGGATGGTGGA
GTGCAGGTGGCGCTGGATGCTATCAAGGCGGCGTCGAATCCCCATCAGTTCCTGGGT
GTGACGAAGCAGGGCCTCACCGCGATCGTGCGAACGCGAGGCAACGACGCGTGCCAC
ATCGTGCTGCGCGGCGGCAAGGGCGGACCCAACTATGACGGGGAGAGCGTACAGAAG
ACGGTCGAGCTGGCGCGCAAGGCCAAGCTCAGCACCTCGATCATGATCGACTGCTCG
CACGACAACTCGCGCAAGAACCACGCCAACCAGCCCATCGTCTCCGCCGCCATCGTA
CGCCAACCGCACGCCCATCGTCTCATCTCTTTCATCATCAAACGCTCACGCACAACA
CGACACACGACACACGACACACAGGCGGAGCAGGTGGCGGCTGGGTGTGCCGACA
TCATCGGAGTGATGATTGAGAGCAACCTCGTCGAGGGCCGACAGGACCTCCCCGCCG
ACGGTCCGCAGTACCTGCAGTACGGGAAGAGCATCACCGACGCGTGCATCAGCTTCA
AGGACACGATCCCCGTGCTCGAGTCCCTCGCCGCGGCCGTGCGAGAACGGAGGAAG

Figure 6

GGCACGTTCCATCCGTTCATCAACGACAAGGAGGTCAAGATCGTGGGCGTGCAGGCG
GCGGGCGAGGGTGTCCATACGGACAAGCACTGCGCGACGCTGGTCAAGGGCACGCCC
GGCGTGCTGCACGGCACGCGCACGATGCTGCTGCAGGACCCCGAGGGCCAGATCAAG
TCCACGCACTCGATCTCGGCCGGGCTGGACTACCCCGGCGTCGGACCCGAGCACGCG
TGGCTGCTCGAGTCGAAGCGCGCCGAGTACGTGGCGGTGAGCGACGAGCAGGCCCTG
GAGGGCTTCAAGGAGCTCACGCGCAAGGAGGGCCTCATGCCGGCCCTGGAGACGTCG
CACGCCGTCTACCACGCCATCCAG

Figure 7

ATCCGAGCGCTGGCGGGCAAGATTCCGATCCTGGGCGTGTGTCTGGGCCACGAGTGT
ATGGTGGAGGAGTACGGCGGCGTGATCGAGCACTGCGGCGAGATCGTGCACGGCAAG
ACCTCCAACATCATTCACGACGGCAAGGGCCTCTACGTCGGTACGCACCCCGTTTA
GATTTATATAACAATTATTATAATTTGTATTTATACATTTAAAAATGCAAACGCTCT
CCGGGCGACAGACATTCCCAACAACGTGCCGGTCATCCGGTATCATTCGCTGGCGGC
GAGGCACACCGCCCTGCCGCCGGACTTTGTTGTGACCTCC

Figure 8

GAGTTCTTGGACACCATCAGCCCGCAGTTCGTGGCCGACCTGGTCTCCTGGGGCGCC
ATCGGAGCGCGCACCACCGAGAGCCAGGTGCACCGCGAGCTAGCCTCCGGTCTGTCC
GTCCCTGTCGGTTTCAAGAACGGTAGGCGCCCTGCCTTGCGTGTGCGTGCGTGCGTG
CGTGTGTGCGTGTGTCCTGTCATCATCGCGGATGGTGCGGGTAGTGAGTCGGTTGTG
TGCGTGTGCGGTGGTGCGTGTGCGTGTGCGGTGGTGCTAATGAGATGGTCC
CGGACCAGGCACGGATGGTGGAGTGCAGGTGGCGCTGGATGCCATCAAGGCGGCGTC
GAATCCCCATCAGTTCCTGGGCGTGACGAAGCAGGGCCTCACCGCGATCGTGCGAAC
GCGAGGCAACGACGCGTGCCACATCGTGCTGCGCGGCGGCAAGGGCGGACCCAACTA
TGACGGGGAGAGCGTGCAGAAGACGGTCGAGCTGGCGCGCAAGGCCAAGCTCAGCAC
CTCGATCATGATCGACTGCTCGCACGACAACTCGCGCAAGAACCACGCCAACCGGCC
CATCGTCTCCGCCGCCATCGTACGCCTACCGCACGCCCTATCTCTGGCATCATCCCA
TGCTCACCCACACACGCACACACTACACAGGCGGAGCAGGTGGCGGCTGGGTGTGCC
GACATCATCGGAGTGATGATCGAGAGCAACCTCGTCGAGGGCCGACAGGACCTCCCC
GCCGACGGTCCGCAGTACCTGCAGTACGGCAAGAGCATCACCGACGCGTGCATCAGC
TTCAAGGACACGGTGCCCGTGCTCGAGTCCCTCGCCGCGGCCGTGCGAGAACGGAGG
AAG

Figure 9

GACGCCAACGAAAACGGCATCCGTTGCATCCTCAACTACGGACACACGATCGGTCAC
GCCATCGAGGCCTTTGCCTTCCCGCTCCTTCTGCACGGAGAGTGCGTGTCGATTGGC
ATGGTACACACGCACGACACACAACACACGCACGCATGCACGCACACACCACCGCAC
GCACGACACACGCGTCATTTTAGTTAACACACGTGGCACGGCGGTACCAGGTGCTCG
AGAGCAAGCTGGCACAGAAGATGAACCACCTCAAGAACCTCAACTTCATTGGCCGGC
TGACGCGATGTCTGCAGGCCTACAAGCTCCCCGTCGTGGTCCCCAAACCGAAGAAAG
TATGTGTGCGTGTGCGTGTGCGGTGGTGCGTGTGCGTGCGTGCGATGCTGGTGACTC
ACCACGTCCACTACCAACAGCAACAGGGCGGCGATCAGGGCAAGCGAAAGGAGGGAA
CGCTCGAATTCACGCCGGAAGACCTGATCAACAAGATGCTCATCGACAAGAAGAACG
CCAACAGCAACATCCGATGCGTGATCGTCAAGGACTTCGGCGATGTGTTCGAACACC
CCGTCGTCGTCGACAAGGACACGCTCAGGTATTCTTCTGCCCTTGTGTGTGTGTT
GTGTGTGTGTGTGTGGTGCGCCTGAGAGCTAAGTGTGACTGGAACAACAGGTTTG
TGCTTTTGCCCTCTGTGGAGGTGGAGCCCACCCAAAGCGGCGTGAGCGGCGTGATCA
CCGTGCCCGGCTCCAAGTCGATCTCCA

Figure 10

```
ATGGACGCCAACGAAAACGGCATCCGTTGCATCCTCAACTACGGACACACGATCGGC
CATGCCATCGAGGCCTTTGCCTTCCCGCTCCTTCTGCACGGAGAGTGCGTGTCGATT
GGCATGGTACGCGCACGACACACAACGCACACGCACGCACACGCGTCATTTCAGTTA
ACACATCGGTTTTTCAATGTGGCACGGCGGTACCAGGTGCTCGAGAGCAAGCTGGCA
CAGAAGATGAACCACCTCAAGAACCTCAACTTCATTGGCCGGCTGACGCGATGCCTG
CAGGCCTACAAGCTCCCCGTCGTGGTCCCCAAACCGAAGAAAGTGCGTGTGCATGTG
TGTGCATGTGTGTGCATGTGTGTGCGGTGTGTGCGGTGTGTGGTGTGTGCGGTGT
GTGCGTGCGATGCTGGTGACTCACATCCACATCCACGACCAACAGCAACAGGGCGGC
GATCAGGGCAAGCGAAAGGAGGGAACGCTCGAATTCACGCCGGAAGACCTGATCAAC
AAGATGCTCATCGACAAGAAGAACGCCAACAGCAACATCCGATGCGTGATCGTCAAG
GACTTCGGCGATGTGTTCGAACACCCCGTCGTTGTTGACAAGGACACGCTCAGGTAT
TCTTCTGCCCTTGTGTATGTGKTGTGTGTGTGTGTGTGTGTCGAGCGCGAGTGTG
TGTCGTGAGCGTGTGTCGTGCGCGTGTGCTCTAATTGCGACTGGACCAACAGGTTTG
TGCTTTTGCCCTCCGTGGCGGTGGAGCCCACCCAGAGCGGCGTGAGCGGCGTGATCA
CCGTGCCCGGCTCCAAGTCGATCTCCAACCGCGTGTTGACTCTTGCCGCCCTGGGCG
AAGGTATGCCACTCTCTCTTCCCTCCTCTCGCCCTTCAGTACATCCAACAAACAAGT
CAAGTTTGACGAACAAACACCACACGCGCGCGCGCGCACACACACACACACACAC
ACACACACACACACACACACTCTGGCTTGCTCGCTTGCACACAGGCGAATGTCAC
ATCAAGGGGCTTCTCTCGGCCGACGACACGGGCGTGATGCTCGCCGCGCTTCGACGA
CTCGGTGTCCAGTACAAGTGGCTCGACCAAGGCCTCGTAAGCGCCTCCCCCCTGCAT
CTGTCTGCCGACAACAGCTCACCCCACCCACCACCCACCACCCGCCGCCGCCAGACG
CTGTACATCAAGGGCAGCGGAGGACAGCTGCAGCCGCCGAAGGAGCCCGAGRTCCCA
TTCTTCCTGGGCAACGCCRGCACGGCGTCGCGCTTCCTGACCACCATGTGCACCCTC
GTCACCCCGCCGGCTGGTACCACCATTTCTCTTGCTTCTCGGCCGGTTCCTTGGCTC
CCCAGTCGACTGTCGACTCATGTCGCTAACCGCCGGCACAGGCTCGACGGAAAAGGT
GTCGACGATCTTGACGGGGGTCGACAGGCTCAAGGGGCGGCCCATCAGCGATCTCGT
GGAGGCGCTGCGGGATGAACGGCTGCGTCATCAACTACCTCGAGAAGGAGGGCTACT
TCCCCATCGAAGTGGTGCGTGCCCTGAGCGCCGATGCGTGTGCGGTGGTGCGTGTGC
GTGTGCGACTGTGTGTGTCGACTAGCGACCAACAACCCCGGGGCTGGCGTCAACTCG
CTCGCAGGTCGGTGGTAAGGGGCTGAACGGTGGTGTGATCAACCTCTCGGCCAAGCT
TAGCAGCCAGTACGTGTCCTCCATCCTTCTCTCGGCCCCGTACGCGCTCAACGACGT
CGACCTGCAGATCAAAGGTGGCCACCCGTCTCTTCCTTGCGTTGTGTCGTGTACGCC
GTGTGCGCCGTGCGCCGTGTGCGTGTGCGTGTGCGCCGTGCGAGTAAACTGAAAGGG
TTCTGCTTTGTATTGGCAGGTGAGGCCGTTTCGCAGCCGTTCATCGAGATGACCATC
AAGGTGATGCAGCAGTTCGGCGTCAAGGTCGTCGACACCTCCAAGGAGGACAAGATC
TCCTGGTTCATCCCCGCGGCGTTTACCACAATCCCAAGGTACCCACCATCACTAGC
CGTCGTGTGTCGTGTGTCGTGGGCTGACTTCTGGTGTCGCGTGCGGTCAGGATTTCG
TCGTCGAGCCCGACGCGTCGTYGCTTCGTACCCTCTCGCGCTGGCGGCCATCACCG
GCGGCGAGATCACTGTGGACAACATCGGCTCGTCGAGCGTGCAGGGCGACGCCCAGT
TCTACACGGTCATGGAGAAGATGGGCTGCACAGTCAACCAGACCACCACCTCCACCA
CCGTGAAGGGTCCGGCGCGCGGTGGCCTGAAGGCCGTCGACATCGACATGTCATCCA
TGACCGACACCTTCATGACCGTCGCAGTCCTCGCCGCCGTCGCCACCGTACGCACAG
GCCCACCGCATTCCTTTCATTCCATTCCAGGCACTGTGCGAGCATGCGCCAAGCAAT
GTTGACAATGTCGTCGACACACACACACACAATACAGGGCACGTCGCGTATTTAC
AACATCGCCAACCAGCGCGTCAAGGAGTGTAATCGCATTGCGGCGATGGTGAAAGAA
CTCGGGAAGTGCGGCGTGACCGCTCGCGAGCTCGAAGACGGTCTGGAGATTGACGGT
TGCGGCGGGGACATCTCCAAGCTGCACGGCGCCAGCATCGAATGCTACAGGGACCAC
```

Figure 10 cont.

```
CGAATTGCCATGAGGTATGCACACGCACCATCGCACACGCTCCACGTGCCTGTGCTT
ATCGTGTGTGTCGTGTGTGTGTCGTGTGTGTCGCGTGTGTGTCGCGTGTAGCTTC
GGCGTGTTCGGAACGGTGGTGCCGGGCATCCTGATCACCGACAAGGAGTGCGTCGAC
AAGACCTACCCCGACTTCTGGTACGACCTCGAGTTCCGCTTCGGCGTCCGCCTGTCC
GTGCCCTCTACCGAGAACGAGCAGCAAAAGCCCGCCGCCGCCGCCACTGCCGAGGCG
TCGGTTGCTGACCGGCCCGGACCGGACGGCGACACCGGTCGGTGGTGCTGGTGGGCA
TGCGCGGGTCAGGCAAGAGCACGATGGGCTCGGCCCTCGCCGCGGGCCTGGGCTGGA
AGTTCATCGACATCGACGTCGAGTTCGAGGCCTTTGTGGGCGAGAAGATCCGGTCCT
TCGTCGACGCGCACGGCTGGCCGGCCTTCCGGGCCAAGGAGGAGGAGCTCGTGCGCC
AGGTGGTCGAGGCCCACCCGCAGCGGACCGTCATCTCCACCGGCGGAGGCATCGTAA
TCTCCCCGACCGCTTTCGAGTACCTCCATTCCC
```

ANTIMICROBIAL COMPOUNDS

FIELD OF THE INVENTION

The present invention relates to compounds that modulate the shikimate pathway and/or a pathway branching from the shikimate pathway in the Amoebida. In particular such compounds may be useful in the treatment or prevention of diseases caused or contributed to by members of the Amoebida Order.

BACKGROUND OF THE INVENTION

*Acanthamoeba* are normally free-living protozoa found throughout the environment. *Acanthamoeba* are responsible for *Acanthamoeba* keratitis and granulomatous Acanthamoeba encephalitis (GAE) in humans (Cohen et al., 1985; Culbertson et al., 1966). *Acanthamoeba* keratitis is normally associated with contact lens wear and is increasingly evident in immunocompetent individuals (Auran et al., 1987; Moore et al., 1985; Stehr-Green et al., 1989).

*Acanthamoeba* (species) are a cause of keratitis and encephalitis in humans. Incidence of *Acanthamoeba* keratitis has been estimated to be 1 per 30000 contact lens wearers per year, although a separate study found that it could be as high as 20, 3.3 and 1.1 per 10,000 for extended wear, daily disposable and rigid gas permeable lenses, respectively. GAE is a disease of the immunocompromised, particularly those with AIDS where it is invariably fatal.

Current therapeutic regimens for *Acanthamoeba* keratitis rely on topical applications of antimicrobials every 15-60 minutes for a period of weeks making treatment arduous. These drugs include a combination of propamidine isothionate and neomycin or chlorhexidine. Current treatments are poorly effective against the cystic stages of the parasite and allow residual infection. Corneal transplantation is often necessary due to extensive damage caused by the parasites prior to diagnosis. Residual cysts remaining after treatment can result in infection of transplanted corneas (Seal, 2003). No effective antimicrobial treatment for GAE has been described although such therapy has been used with apparent effect as an adjunct to surgery (Marciano-Cabral et al., 2000; Seijo Martinez et al., 2000). This exemplifies the urgent need for new and effective antimicrobials.

The present inventors have now obtained evidence that the shikimate pathway occurs in *Acanthamoeba* and that inhibition of this pathway is capable of restricting the growth of the parasite in vitro. The shikimate pathway is essential for production of a plethora of aromatic compounds in plants, bacteria and fungi. The shikimate pathway was at one time believed to be absent from all protozoans, but was recently demonstrated to be present in Apicomplexan parasites. (Roberts et al., 1998).

The shikimate pathway results in the production of chorismate. In the first instance the shikimate pathway converts phosphenolpyruvate and erythrose 4-phosphate to chorismate generally in seven enzyme-catalysed steps. The shikimate pathway feeds numerous other pathways with essential compounds. In particular the shikimate pathway provides compounds for use in pathways producing ubiquinone, folate, and/or aromatic amino acids in the Amoebida. By way of an example, chorismate, produced by via the shikimate pathway, is fed into pathways for synthesising ubiquinone and folate. The synthesis of ubiquinone from chorismate depends upon eight enzymes while the production of folate in the Amoebida results from the conversion of chorismate to tetrahydrofolate in six enzymatic reactions.

In addition to the above detailed pathways, chorismate is also used in pathways, which result in the synthesis of aromatic amino acids, for example tryptophan, phenylalanine and tyrosine. Tryptophan synthesis from chorismate depends upon seven enzymes. Phenylalanine and tyrosine synthesis involve separate pathways that branch from prephenate, which is produced from chorismate via the action of chorismate mutase. The pathways that lead to either phenylalanine or tyrosine, each involve an additional five enzymes (reviewed, Roberts et al., 2002).

The molecular organisation of the shikimate pathway enzymes differs between taxonomic groups (Coggins et al., 1987). Most prokaryotes have monofunctional polypeptides encoded by separate genes, which provide seven single enzyme activities. Plants have a molecular arrangement similar to prokaryotes (Butler et al., 1974), with the exception of dehydroquinase (DHQase) and shikimate dehydrogenase, which are present as separate domains on a bifunctional protein (Mousdale et al., 1987). At least one prokaryote, *Chlaniydia*, also has this bifunctional fusion. All fungi examined to date have mono-functional 3-deoxy-D-arabino-heptulosonate 7-phosphate (DAHP) synthases and chorismate synthases and a pentafunctional polypeptide termed AROM (Duncan et al., 1987). The AROM polypeptide has domains analogous to the bacterial enzymes; dehydroquinate (DHQ) synthase, EPSP synthase, shikimate kinase, DHQase and shikimate dehydrogenase.

The shikimate pathway is absent from mammals, including humans that must obtain their aromatic compounds from their diet (Roberts et al., 1998; Roberts et al., 2002). This makes this pathway a potentially excellent target for new antimicrobial agents. The present inventors have found evidence that the shikimate pathway occurs in *Acanthamoeba*.

As a result it is among the objects of the present invention to provide an antimicrobial compound which is effective against the Amoebida.

SUMMARY OF THE INVENTION

In a first aspect of the present invention there is provided a use of a compound for modulating the shikimate pathway and/or any pathway branching from the shikimate pathway in the Amoebida.

The Amoebida is an Order within the Phylum Protozoa, which comprises the Vahlkampfidae, the Pelomyxidae, the Paramoebidae, the Mastigamoebidae, the Hartmannellidae, the Flabellulidae, the Entamoebidae, the Amoebidae and the Acanthamoebidae Families.

Conveniently, compounds of the present invention may modulate the shikimate pathway and/or a pathway branching from the shikimate pathway in the Acanthamoebidae. Generally the compounds of the present invention modulate said pathways in *Acanthamoeba*, specifically for example *Acantiamoeba castellanii* and *Acanthamoeba polyphaga*.

By "branching" it is meant a pathway that metabolises a particular product derived from the shikimate pathway.

The products of the shikimate pathway, for example chorismate, or the products of any pathway branching from the shikimate pathway, for example ubiquinone, folate or aromatic amino acids, are essential components of a number of biological systems in the Amoebida. Consequently compounds of the present invention capable of modulating the shikimate pathway and/or a pathway branching from the shikimate pathway may also be expected to have an effect upon the ability of the Amoebida to grow and/or survive.

Typically compounds of the present invention may modulate the shikimate pathway or a pathway branching from the shikimate pathway to an extent that the growth of the Amoebida is inhibited (i.e. microbistatic (amoebidastaic)). Additionally or alternatively said compound may cause the Amoebida to die (i.e. microbicidal (amoebidacidal)).

Conveniently, compounds of the present invention may modulate an enzyme or enzymes of the shikimate pathway and/or an enzyme or enzymes of a pathway branching from the shikimate pathway, in the Amoebida. For example a compound of the present invention may inhibit a particular enzyme of the shikimate pathway and/or of a pathway branching from the shikimate pathway.

Enzyme inhibitors are well known to one of ordinary skill in the art. Enzyme inhibitors may be classified as, for example, specific, non-specific, reversible, non-reversible, competitive and non-competitive. In the present invention any compound capable of inhibiting any enzyme or enzymes of the shikimate pathway or any enzyme or enzymes of a pathway branching from the shikimate pathway, may potentially be used to modulate the production of chorismate, ubiquinone, folate and/or aromatic amino acids in the Amoebida.

By "inhibition" it is meant that, when compared to an enzyme which has not been contacted and/or exposed to a compound which might inhibit its activity, the rate at which an enzyme catalyses the production of a particular compound from a particular substrate is reduced.

Typically the compound for use in modulating the shikimate pathway and/or a pathway branching from the shikimate pathway in the Amoebida, may be a specific or non-specific enzyme inhibitor. It should be understood that the term non-specific refers to a compound, the effects of which are not restricted to a particular enzyme, or class of enzyme, but which generally affects the activity of substantially all enzymes. In contrast, the term specific inhibitor may be taken to refer to a compound which may inhibit a particular enzyme but which has no effect on the activity of another enzyme.

Typically non-specific inhibitors may function as a result of the fact they denature by means of a change in temperature, pH or the like. However, non-specific inhibitors may also irreversibly bind to and block the active site of an enzyme thus preventing it from functioning to catalyse the production of a particular compound. Specific enzyme inhibitors may function by means of binding to a particular enzyme and causing either the active site to be blocked or the enzyme to undergo a conformational change such that it can no longer receive and catalyse the conversion of a particular substrate.

The term competitive inhibitors may be taken to comprise compounds which are capable of occupying the active site of a particular enzyme resulting in the exclusion of the correct substrate. In this way the rate at which a particular enzyme is able to catalyse the production of a particular compound is reduced. Such compounds may closely resemble the particular substrate of the enzyme.

In the present case, compounds for use in modulating the shikimate pathway and/or a pathway branching from the shikimate pathway in the Amoebida, may also include competitive inhibitors of each of the enzymes involved in the shikimate pathway and/or a pathway branching from the shikimate pathway. Generally such compounds may structurally resemble the native (natural/correct) substrate of the enzyme. Alternatively, a competitive inhibitor may comprise a peptide which, for example may, bind to the active site or substrate binding domain of an enzyme and block substrate binding.

Conveniently said compounds may be small organic molecules capable of modulating the function of an enzyme or enzymes of the shikimate pathway and/or a pathway branching from the shikimate pathway. Typically the small organic molecule may be an analogue of any of the substrates of the enzymes utilised in such pathways. Conveniently the substrate analogue may be modified in such a way so as to either inhibit and/or prevent the progression of a particular enzymatic reaction in a particular pathway.

In addition or alternatively, a compound for use in modulating the shikimate pathway and/or a pathway branching from the shikimate pathway in the Amoebida, for example a small organic enzyme substrate analogue, may interact with a particular enzyme or enzymes which in turn catalyse the production of a product which is incapable of being utilised by another enzyme of the shikimate pathway and/or a pathway branching from the shikimate pathway. In this way further enzymatic reactions will not be possible and the pathway will be unable to progress.

The use of a modified substrate analogue may directly or indirectly prevent the production of a particular component of the shikimate pathway and/or a pathway branching from the shikimate pathway. As such a modified substrate analogue as substantially described above, may directly or indirectly modulate the production of chorismate, ubiquinone, folate and/or aromatic amino acids in the Amoebida.

The term non-competitive inhibitor may be taken to include those compounds which affect the rate at which an enzyme catalyses the production of a particular compound. In contrast to the competitive inhibitors, non-competitive inhibitors may interact with an enzyme at a position other that the active site of an enzyme. For example a non-competitive inhibitor may bind to an enzyme and induce a conformational change in the enzyme such that the binding site of the enzyme may no longer receive a substrate.

For example a small organic molecule may modulate an enzyme of the shikimate pathway in the Amoebida and thus the production of chorismate, by, for example, specifically inhibiting the activity of EPSP synthase which catalyses the conversion of shikimate-3-p to 5-0-(1-carboxyvinyl)-3-phosphoshikimate. An example, of a compound for use in specifically inhibiting the production of EPSP synthase is N-(phosphonomethyl)glycine ($C_3H_8NO_5P$) or glyphosate.

It should be understood that compounds related to glyphosate are known in the art and therefore are likely to be useful as compounds for use in the modulation of the shikimate pathway and/or a pathway branching from the shikimate pathway in the Amoebida. Such compounds are detailed in US2003186352 to Roberts et al as well as US2004198606 to Bonnet et al. For example inhibitors related to glyphosate may include sulfosate and a modified precursor for EPSP.

Thus there is provided use of glyphosate for the modulation of the shikimate pathway and/or a pathway branching from the shikimate pathway in the Amoebida.

By contacting glyphosate or a related compound with an Amoebida it may be possible to inhibit EPSP synthase of the shikimate pathway. As a result chorismate, produced by the shikimate pathway, may not be available for use by the ubiquinone, folate and/or aromatic amino acid synthesis pathways. This will potentially have the affect of preventing the production of chorismate, ubiquinone, folate and/or aromatic amino acids which in turn may have a detrimental effect upon the growth of the Amoebida.

The present invention may also provide a composition for use in modulating the shikimate pathway and a pathway branching from the shikimate pathway, wherein the composition comprises a compound capable of modulating the activity and/or expression of an enzyme of the shikimate pathway and a compound capable of modulating the activity and/or expression an enzyme of a pathway branching from the shikimate pathway. For example the composition may comprise a compound capable of modulating the ubiquinone, folate or aromatic amino acid pathway in the Amoebida.

By way of an example of such a composition, it may be possible to combine a compound capable of modulating an enzyme of the shikimate pathway with a compound capable of modulating an enzyme of the folate pathway.

Compounds potentially useful in the modulation of enzymes of the folate pathway may include, for example, sulphonamides, pyrimethamine or any other compound known to interfere with folate synthesis.

Other examples of folate inhibitors include, proguanil and cycloguanyl or trimethoprim and a number of derivatives (Sirichaiwat et al. 2004). Further examples include the triazine exemplified by WR99210 and the prodrug PS-15 (Kinyanjui et al. 1999).

In a further embodiment of the present invention compounds for use in modulating the shikimate pathway and/or a pathway branching from the shikimate pathway in the Amoebida, may also include oligonucleotide sequences. Such compounds may modulate the expression and/or activity of enzymes of the shikimate pathway or enzymes of pathways branching from the shikimate pathway.

Conveniently such oligonucleotide sequences may be complementary to sections of the genome of a member of the Amoebida Order, which encode enzymes involved in the shikimate pathway and/or a pathway branching from the shikimate pathway in the Amoebida.

Generally the oligonucleotide sequences may be sequences of nucleic acid, either DNA or RNA which interfere with the functional sequences encoding the enzymes of the shikimate pathway and/or a pathway branching from the shikimate pathway in the Amoebida.

Accordingly the oligonucleotide sequences may be sections of messenger or ribosomal RNA (rRNA) which interfere with the RNA transcripts of the functional enzyme genes. Such oligonucleotides are referred to in the art as interfering RNA (iRNA), short interfering RNA (siRNA) or antisense oligonucleotides. Algorithms such as BIOPREDsi may be used to computationally predicts siRNA sequences that have an optimal knockdown effect for a given gene.

In a second aspect of the present invention there is provided use of a compound capable of modulating the shikimate pathway and/or a pathway branching from the shikimate pathway in the Amoebida for the preparation of a medicament for the treatment of diseases caused and/or contributed to by the Amoebida.

For example, diseases which are potentially treatable with such a medicament, may include keratitis and/or encephalitis, specifically granulomatous *Acanthamoeba* encephalitis (GAE) in humans.

In a third aspect of the present invention there is provided a method of treating a subject suffering from a disease caused and/or contributed to by the Amoebida, said method comprising the step of;
 a) administering to a subject a therapeutically effective amount of a compound capable of modulating the shikimate pathway and/or a pathway branching from the shikimate pathway in the Amoebida.

In a fourth aspect of the present invention there is provided a pharmaceutical formulation comprising a compound capable of modulating the shikimate pathway and/or a pathway branching from the shikimate pathway for use in treating keratitis caused or contributed to by a member of the order Amoebida, in association with a pharmaceutically acceptable carrier or diluent.

Said pharmaceutical formulation may be formulated, for example, in a form suitable for topical administration. For example the formulation for topical administration may be presented as a solution or a suspension in an aqueous or non-aqueous liquid, or as an oil-in-water liquid emulsion.

Conveniently the pharmaceutical formulation may be packaged within a receptacle to allow direct application to the eye. For example the pharmaceutical formulation may be packaged within a receptacle capable of delivering a predetermined volume of the formulation to the site of infection, for example the eye. Such receptacles are well known in the art and may include receptacles such as those used to deliver fluids, for example pharmaceutical formulations, to the eye.

In a fifth aspect of the present invention there is provided a composition for cleaning contact lenses and/or storing contact lenses, said composition comprising a compound capable of modulating the shikimate pathway or a pathway branching from the shikimate pathway.

Such a composition may be effective in reducing the incidence of ocular infections caused and/or contributed to by members of the Order Amoebida, for example *Acanthamoeba castellanii* and *Acanthamoeba polyphaga*.

Conveniently the composition may be a solution used to clean contact lenses during periods when they are not in use. The composition may, for example, comprise a neutral saline solution and a compound capable of modulating the shikimate pathway or a pathway branching from the shikimate pathway. The composition may, for example, comprise glyphosate or a compound related to glyphosate. Additionally or alternatively the composition may comprise any of the enzyme inhibitors substantially described above.

In this way contact lenses that have been worn for a period of time by a subject may be removed and immersed in a said composition so as to reduce the incidence of any Amoebida present on the contact lenses.

In a sixth aspect of the present invention there is provided a receptacle containing at least one contact lens and a solution, said solution comprising a compound capable of modulating the shikimate pathway and/or a pathway branching from the shikimate pathway and.

Preferably the receptacle is sealed such that the contents remain sterile until the receptacle is opened.

In a further aspect of the present invention there is provided a method of detecting an Amoebida in a sample, said method comprising the steps of;
 a) providing a sample; and
 b) detecting the presence of any gene and/or protein of the shikimate pathway or a pathway branching from the shikimate pathway in the Amoebida.

A "sample" may comprise cells derived from a subject suspected of being infected with an Amoebida. Generally the cells should be derived from an appropriate area of the subject, for example if the subject is suspected of suffering from keratitis, a swab or other sampling device may be used to obtain a sample from the surface of, for example, the cornea of the eye.

Alternatively or additionally a sample may comprise a fluid obtained from the subject. Fluids suitable in the presently described method may include, for example, whole blood, serum, plasma, cerebral spinal fluid (CSF), saliva or tears.

There are many techniques known in the art, which permit the detection of a gene or protein in a sample. Generally the detection of genes involves the extraction of nucleic acid from a sample and a subsequent amplification process such as polymerase chain reaction (PCR) or reverse transcriptase PCR (RT-PCR) or real-time PCR. Thus, once a sample of nucleic acid has been obtained, it may be possible to specifically amplify and detect genes from the shikimate pathway and/or a pathway branching from the shikimate pathway.

The products of such an amplification process may be resolved using techniques such as agarose gel electrophoresis. The resolved products may either be visualised directly, by means of addition of a fluorescing intercalating agent such as ethidium bromide, or they may be transferred to another substrate, for example nitrocellulose. Once transferred to an alternative substrate such as nitrocellulose, the resolved products may be probed with a short oligonucleotide sequence specific for a certain sequence. Such probes are readily designed from sections of known sequence. In the present case, oligonucleotide probes designed to react specifically with the sequences which encode genes involved in the shikimate pathway or a pathway branching from the shikimate pathway, may be used to detect Amoebida specific sequences in a particular sample.

Oligonucleotide probes bound to a particular sequence may be identified by means of a label conjugated to the probe, or to a secondary probe. Such labels may be chemiluminescent, fluorescent or radioactive.

Methods for the extraction of proteins are also well known in the art and include techniques such as affinity and size exclusion chromatography, immunoprecipitation and the like. In the present case proteins may be extracted from the sample obtained from the subjected suspected of having an Amoebida infection. Said proteins may then be resolved by means of native or denaturing SDS-polyacrylamide gel electrophoresis. Proteins resolved in this manner may be visualised directly with non-specific protein stains such as, for example, silver stain, Coomassie blue stain, colloidal blue and colloidal gold stains. Additionally or alternatively the proteins may be transferred to another substrate, such as nitrocellulose, and probed with a molecule, for example an antibody specific for a particular protein or proteins. Conveniently the molecule used to probe the resolved and transferred proteins may be specific for a particular protein produced by a member of the Amoebida Order.

A molecule used to probe proteins for proteins specific to the Amoebida may be labelled with a compound to allow detection of bound molecule. Molecules may be conjugated to compounds which are fluorescent, chemiluminescent or radioactive.

In order to interpret the results it may be desirable to obtain a "control" sample from a subject not infected with an Amoebida. Said control sample may be subjected to the same nucleic acid or protein extraction protocol as substantially described above. The results obtained may be compared with those obtained from a person suspected of being infected with an Amoebida. Detection of Amoebida specific sequences in a sample derived from a subject suspected of being infected with a member of the Amoebida Order, may indicate that the subject was indeed infected with such an organism.

In a another aspect of the present invention there is provided a method of identifying a compound which is capable of modulating the enzymes of the shikimate pathway and/or the enzymes of any pathway branching from the shikimate pathway in the Amoebida, said method comprising the steps of;

(a) contacting an agent with a system capable of expressing one or more enzymes of the shikimate pathway and/or pathways branching from the shikimate pathway from an Amoebida species; and (b) detecting any modulation of expression and/or activity of said one or more enzymes of the shikimate pathway and/or pathways branching from the shikimate pathway.

The term "agent" may be taken to encompass a number of different types of compound. For example, an agent may comprise a small organic molecule such as a chemical compound. Additionally or alternatively, an agent may comprise an amino acid, a peptide or a protein. Such molecules may be obtained from chemical or protein libraries. Furthermore it is envisaged that "agents" which comprise nucleic acids, for example RNA or DNA (as described above), may also be tested by the above method.

It is to be understood that "system" refers to both cell-free and cell-based systems. The "system" may comprise an enzyme or enzymes derived from the shikimate pathway and/or a pathway branching from the shikimate pathway. In addition, the system may also comprise a substrate or substrates which said enzyme or enzymes interact with. Cell based systems may be created by, for example, cloning components of the shikimate pathway and/or a pathway branching from the shikimate pathway into cells derived from organisms which do not normally express the shikimate pathway or any of the pathways branching from the shikimate pathway. Alternatively, test agents may be added to cells which normally comprise the shikimate pathway or pathways which branch from the shikimate pathway. A control system is a system as described above but which has not been exposed to the test agent and as such may be considered to provide a result which indicates the normal level of activity and/or expression of a particular enzyme or enzymes.

The term modulation is used to describe an increase or decrease in enzymatic activity and/or an increase or decrease in enzyme expression when compared to the activity or expression of the same enzyme which has not been exposed to the test agent.

The techniques used to detect the modulation of activity of enzymes of the shikimate pathway or pathways branching from the shikimate pathway include those described in the following documents by Mousdale and Coggins (1985), Hawkes et al., (1990), Nichols and Green (1992) and Roberts et al., (1998). Thus after a system has been contacted with an agent to be tested, these assays may be used to determine whether or not the activity of a particular enzyme or enzymes has been modulated by the agent.

Modulation of expression may be detected by, for example, creating a fusion protein comprising an enzyme of the shikimate pathway and/or an enzyme of a pathway branching from the shikimate pathway and a detectable tag, for example Green Fluorescent Protein (GFP) or some other chemiluminescent, bioluminescent or fluorescent tag. Other forms of tag include, for example, His and GST tags which may be detected by means of an antibody or the like. In this way, an increase enzyme expression would result in an increase in the amount of tag detected when compared to a system comprising the same fusion protein but which has not been exposed to the test agent. Additionally or alternatively, the level of expression of an enzyme or enzymes may also be determined by means of quantifying the amount of specific mRNA present, Methods for quantifying the amount of a particular mRNA include quantitative real-time PCR, agarose gel electrophoresis and/or Northern/Southern blotting.

Current assays used to determine the efficiency of potential *Acanthamoeba* inhibitors include manual counting using a haemocytometer (Connor et al. 1991) or staining with fluorescent viability dyes and flow cytometric analysis (Khunkitti et al. 1997: Borazjani, et al. 2000). Other quantitative methods include the standard plaque assay (Khunkitti et al 1997; Hugo et al. 1991) and a quantitative microtitre method for the enumeration of track forming units (Buck, S. L., and R. A. Rosenthal, 1996). The number of viable organisms has also

DETAILED DESCRIPTION OF THE INVENTION

The present invention will now be described by way of example and with reference to the figures which show:

FIG. 2. The cDNA sequence of *A. castellanii* DHQS and partial EPSP synthase.

FIG. 3. The predicted amino acid sequence of *A. castellanii* DHQS and partial EPSP synthase.

FIG. 4. Partial cDNA sequence of *A. castellanii* chorismate synthase.

FIG. 5. Partial cDNA for DAHP synthase sequence from *A. castellanii*.

FIG. 6. Partial cDNA for Tryptophan synthase Beta subunit from *A. castellanii*.

FIG. 7. Partial gDNA for Anthranilate synthase from *A. castellanii*.

FIG. 8. Partial gDNA for DAHP from *A. polyphaga*

FIG. 9. The cDNA sequence of *A. polyphaga* DHQS and partial EPSP synthase.

MATERIALS AND METHODS

*Acanthamoeba castellanii* and *Acanthamoeba polyphaga*.

*Acanthamoeba polyphaga* (Strain No. 1501/18) were obtained from CCAP (Cumbria, UK). *Acanthamoeba castellanii* (Neff strain) was kindly obtained from Keith Vickerman (Glasgow, UK). *A. castellanii* and *A. polyphaga* trophozoites were grown in (a) Rich media containing 20% mycological peptone (Fluka, UK) and 0.9% maltose (Sigma, UK) and supplemented with 1% Penicillin, Streptomycin and Amphotericin B (All Sigma, UK) or (b) modified 11 containing 20% Rich media. *Acanthamoeba* spp. were incubated at room temperature in 75 cm$^2$ tissue culture flasks until 90-95% confluence, then harvested or sub-cultured using Accutase (Sigma, UK).

80% Modified M11 (L-Arginine 0.825 g/L, L-Methionine 0.3 g/L, L-Leucine 0.9 g/L, L-Isoleucine 0.6 g/L, L-Valine 0.7 g/L, Glycine 1.5 g/L, L-LysineHCl 1.25 g/L, L-Threonine 0.5 g/L, Glucose 18 g/L, Sodium Citrate 1.0 g/L Biotin 0.25 mg/L, B$_{12}$ 0.00125 mg/L, ThiamineHCL 1.25 mg/L, ZnSO$_4$.7H$_2$O 1 mg/L, MnCl$_2$.4H$_2$O 2.3 mg/L, (NH$_4$)$_6$MO$_7$O$_{24}$.4H$_2$O 0.4 mg/L, CoCl$_2$ 0.017 mg/L, CuSO$_4$.5H$_2$O 0.0033 mg/L, H$_3$BO$_3$ 0.1 mg/L, EDTA 0.01 mg/L, MgSO$_4$.7H$_2$O 0.985 g/L, CaCl$_2$.2H$_2$O 0.0588 g/L, (NH$_4$)$_2$SO$_4$FeSO$_4$.6H$_2$O 0.0196 g/L, NaHPO$_4$.2H$_2$O 0.445 g/L, KH$_2$PO$_4$ 0.34 g/L), 20% peptone media (mycological peptone, 200 g/L, maltose 9 g/L)

The susceptibility of the *A. castellanii* to glyphosate as assessed by the almarBlue assay. The susceptibility of *A. castellanii* to glyphosate was determined by a modification of the method described by McBride et al., (2005). *A. castellanii* cells were grown in 75 cm$^2$ flasks until 90-95% confluence and harvested using Accutase (Sigma, UK). *A. castellanii* and *A. polyphaga* cells were seeded in triplicate at 1×10$^4$ cells per well in 50 µL of medium in 96 well tissue culture plates (Greiner, UK) and allowed three hours to adhere. 50 µL and 200 µL of medium containing glyphosate (Sigma Poole, UK), in the range 9 mM to 0.27 µM, was freshly prepared and added to the wells containing cells. Test plates were incubated for 96 hours in normal culture conditions. Six hours prior to the end of incubation 10 µL of alamarBlue reagent was added to the test wells of the 96 well plate. Test plates were incubated for 6 hrs at room temperature in the dark. AlamarBlue reduction was assessed as previously described. The percent inhibition of almarBlue reduction was calculated using the formula:

$$\frac{(\epsilon ox)\lambda A\lambda_1 - (\epsilon ox)\lambda_1 A\lambda \text{ of treated } Acanthamoeba}{(\epsilon ox)\lambda A°\lambda_1 - (\epsilon ox)\lambda_1 A°\lambda \text{ of untreated } Acanthamoeba} \times 100$$

[where: $°\lambda_1$=absorbance of untreated control with alamarBlue at 570 nm); $°\lambda_2$=absorbance of untreated control with alamarBlue at 600 nm)].

This number was subtracted from 100 to give percent alamarBlue reduction relative to untreated control cultures.

Degenerate PCR for the Shikimate Pathway Genes in *A. castellanii*

Degenerate primers were designed to amplify a portion of DHQS from *Acanthamoeba* cDNA (AcDHQSdegF, 5'-GGY GGY GGY GTI ATY GGY G-3' and AcDHQSdegRl, 5'-TCV GCY TCC TTI ACC ATR CC-3')

5' RACE for the Shikimate Pathway Genes from *A. castellanii*

5' RACE was performed using a 5', 3' RACE kit (Roche Molecular Biochemicals, UK). 5'RACE was performed using the 5'/3'RACE kit according to the manufacturer's instructions (Roche Molecular Biochemicals). First strand cDNA was synthesized from 2 µg total RNA using 25 pmol of a gene-specific primer, 10 U of AMV reverse transcriptase and 10 mM of each dNTP and in 1× cDNA synthesis buffer (50 mM Tris-HCl, 8 mM MgCl$_2$, 30 mMKCl, 1 mM dithiothreitol, pH8.0) in a final volume of 20 µl. The reaction was incubated for 60 minutes at 55° C. and for a further 10 minutes at 65° C.

The cDNA was subsequently purified by the High Pure PCR Product Purification Kit (Roche Molecular Biochemicals) according to the manufacturer's instructions and eluted in 50 µl 10 mM Tris-HCl, pH8.3.

A dA-tail was attached to the 5'end of the first strand cDNA by incubating 19 µl of the purified cDNA sample with 2.5 µl 10× reaction buffer (100 mM Tris-HCl, 15 mM MgCl$_2$, 500 mM KCl, pH8.3) and 2 mM dATP for 3 minutes at 94° C. After being chilled on ice 10 U of terminale transferase was added and the reaction was incubated for 20 minutes at 37° C. and terminated at 70° C. for 10 minutes.

Nested PCR was performed to amplify the unknown region obtained from 54 µl of dA-tailed cDNA in a 25 µl reaction containing 0.5 µl oligodT-anchor primer (5'-GAC CAC GCG TAT CGA TGT CGA CTT TTT TTT TTT TTT TTV-3' V=A, C or G), 25 pmol of a second gene-specific primer designed upstream from the first, 10 mM of each dNTP, 1 U of Expand High Fidelty Taq polymerase (Roche Molecular Biochemicals) and IX reaction buffer. The following temperature cycling conditions were used. Denaturation at 94° C. for 2 minutes, followed by 10 cycles of denaturation at 94° C. for 15 seconds, annealing at 55° C. unless stated otherwise and elongation at 72° C. for 40 seconds. This was repeated for a further 25 cycles, but 20 seconds for each cycle were added onto the elongation step. A final elongation step was at 72° C. for 7 minutes.

A second round of nested PCR was usually necessary to obtain the desired result, under the same conditions from 1 µl of a 1:20 dilution of purified PCR product from the first nested PCR. This employed a third gene-specific primer designed further upstream from the second together with the oligodT-anchor primer. The final product was run on a 1.5% agarose gel, purified and cloned into pDRIVE for sequencing previously as described.

Custom RACE primers were designed from the sequence of DHQS obtained by degenerate PCR (5'RACE1, 5'-GGA TGC CGT TTT CGT TGG CGT C-3'; 5'RACE2, 5'-CTG TCG CTC CTC AAA ACT C-3'; 5'RACE3; 5'-TAG ACT GCC TTG GGG TGG TGG-3')

Genome Walking for the Shikimate Pathway Genes from *A. castellanii*.

Genome walking was used to obtain portions of the DHQS genomic sequence and to obtain further portions of genomic DNA. Long-Distance Genome Walking PCR, adaptation of asymmetric PCR was used in order to isolate the unknown 5' genomic sequence of GRA3b adjacent to the known sequence. The method used was as described by Min and Power (1997). Initially the known sequence of DHQ synthase was extended by asymmetric PCR from 50 ng of gDNA using 50 pmols of a gene-specific reverse primer GW1 in a 50 µl reaction containing, 2.5 U of Expand High Fidelity Taq polymerase, 5 µl of 10× Expand High Fidelity Taq polymerase with $MgCl_2$ (Roche Molecular Biochemicals, Germany) and 0.2 mM of each dNTP (Promega, UK). Conditions for PCR were 35 cycles of denaturation at 96° C. for 10 seconds, annealing at 64° C. for 10 seconds, and extension at 68° C. for 4 minutes. The single-stranded gDNA (ssgDNA) product was purified using the PCR purification kit (Qiagen, USA) and eluted in 30 µl of 10 mM Tris-HCl, pH8.3 and adjusted to a volume of 10 µl by centrifugal evaporation. The ssgDNA was incubated at 95° C. for 5 minutes and immediately chilled on ice for 2-3 minutes.

A dC-tail was added to the unknown 5'end with the DNA tailing kit (Roche Molecular Biochemicals). 4 µl of 5× tailing buffer (1M potassium cacodylate, 125 mMTris-HCI, 1.25 mg/ml BSA, pH6.6), 3 µl of 5 $mMCoCI_2$, 1 µl of 100 pmol dCTP and 50 U of terminal deoxyribonucleotidyl transferase were added to 4 µl of the purified ssgDNA and incubated at 37° C. for 20 minutes followed by incubation at 70° C. for 10 minutes.

5 µl of the tailing reaction was used in a nested PCR containing the reagents used in the initial extension step. Primers used were the gene-specific reverse primer GW2, designed upstream from GW1 and a oligodG-anchor primer (5'-CGA GGA ATT CGG GGG GGG GGG G-3'), engineered to contain an EcoRI site near its 5' end. Cycling conditions were 40 cycles of denaturation at 96° C. for 30 seconds, annealing at 65° C. for 15 seconds and extension at 68° C. for 5 minutes. A final extension was at 65° C. for 5 minutes. The product was run on a 1% agarose gel, purified and cloned into pDRIVE for subsequent sequence analysis.

Following sequencing of the product a second round of genome walking was performed by repeating this procedure, but substituting GW1 and GW2 primers with GW3 and GW4 primers. A third round of genome walking was performed with primers GW5 and GW6 based on the sequence obtained with primers GW3 and GW4.

Primers were: GW1, 5'-ATG GAC GCC AAC GAA AAC G-3', GW2, 5'-TTG ACA AGG ACA CGC TCA GG-3'; GW3, 5'-TGT CAC ATC AAG GGG CTT CTC-3'; GW4, 5'-AAC GGC TGC GTC ATC AAC TAC C-3'; GW5, 5'-ACTGTG-GACAACATCGGCTCG-3'; GW6, 5'-TCTGGAGAT-TGACGGTTGCG-3'.

Mining the *Acanthamoeba* Genome Project for the Shikimate Pathway Genes

The *Acanthamoeba* genome project http://www.tigr.org/ was interrogated, using the tBLASTn algorithm and known protein sequences, for DNA sequences with the potential to encode shikimate pathway enzymes or enzymes that are involved in the synthesis of tryptophan, phenylalanine or tyrosine. Where sequences with potential to code for these enzymes were identified, PCR primers were obtained and the sequences amplified, cloned and verified. From these searches, sequences for chorismate synthase and DAHP synthase were identified and primers designed (DAHP synthase: DAHPFOR, 5'-GAG TTC TTG GAC ACC ATC AGC-3'; DAHPREV, 5'-CTT CCT CCG TTC TCG CAC GGC CGC-3' and Chorismate synthase:
CSFOR, 5'-ATG ACG AGC TTT GGC AGA GCG-3'; CSREV, 5'-CGT CTT CTG CGC CTG GCT AAT C-3').

Partial sequences for the 2 enzymes involved in tryptophan synthesis, Tryptophan synthase beta subunit and Anthranilate synthase were identified and primers designed. (Tryptophan synthase: TryptSFor, 5' GGC ACG TTC CAT CCG TTC ATC-3'; TryptSRev CTG GAT GGC GTG GTA GAC GGC and Anthranilate synthase: AnthranSFor, 5' ATC CGA GCG CTG GCG GGC AAG-3'; AnthranSRev, 5'-GGA GGT CAC AAC AAA GTC CGG C-3').

Results

Susceptibility of *A. castellanii* to Glyphosate

Figure 1:
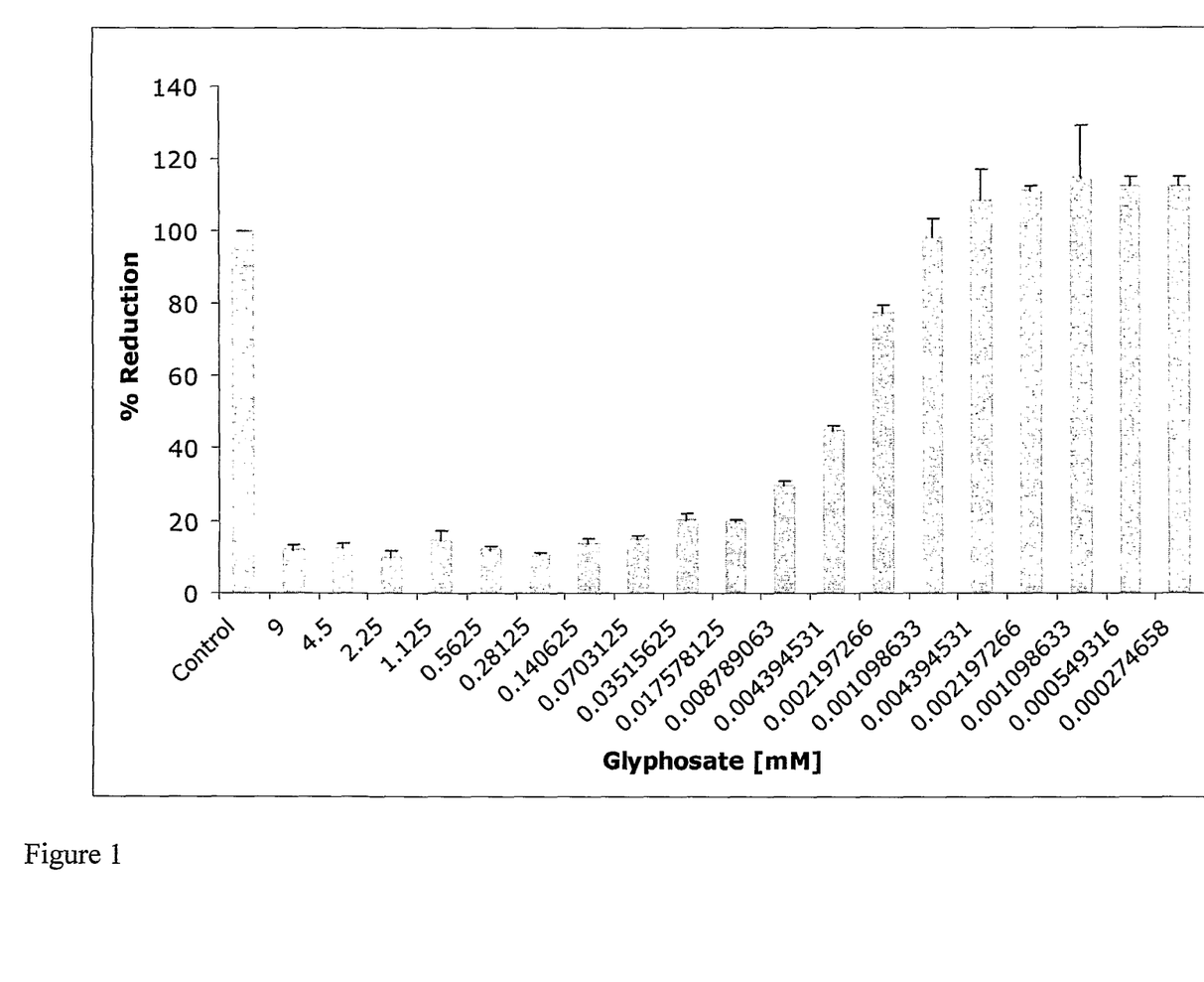
FIG. 1. Glyphosate inhibition of *A. castellanii* over a 96 hr period as determined by percent alamarBlue reduction relative to untreated control cultures.

Glyphosate was found to inhibit *A. castellanii* in a dose dependent manner with an IC50 between 0.00439 and 0.00219 mM (FIG. 1).

Degenerate PCR and 5' RACE Yields a Portion of DHQS

Degenerate PCR gave a portion of the DHQS cDNA. This was extended in the 5' direction by 5' RACE, which gave a putative initiation codon.

Genome Walking Yields a Portion of the DHQS Gene that Extends into a Region that Encodes a Predicted EPSP Synthase Providing Evidence of a Pentafunctional AROM Polypeptide in *Acanthamoeba*.

Figure 10:
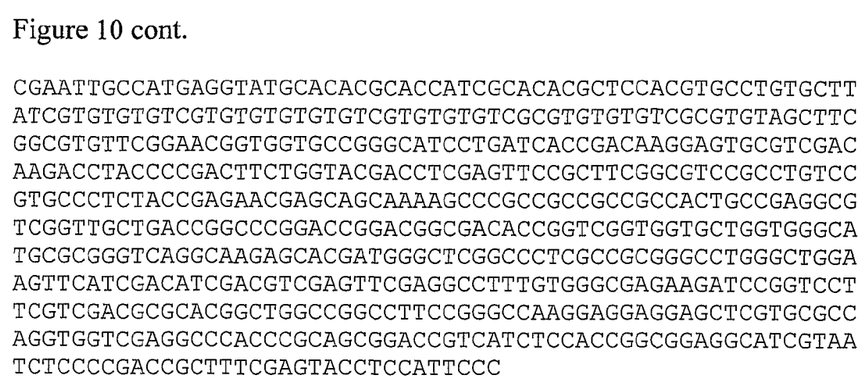
FIG. 10. Partial gDNA sequence of DHQS, EPSP synthase and Shikimate kinase from *A. castellanii*.

Two successive rounds of genome walking gave specific products that when cloned and sequenced were found to have areas of predicted homology with previously identified DHQ synthases and EPSP synthases. That the genome walking products and the original degenerate PCR product were contiguous was confirmed by amplifying a portion of cDNA from the initiation codon to within the EPSP synthase using the primer: DHQSfor 5'-GAC GCC AAC GAA AAC GGC ATC C-3' and EPSPrev, 5'-TGG AGA TCG ACT TGG AGC CCG GG-3' (FIG. 2). The predicted polypeptide sequence this cDNA codes for has considerable homology with the DHQS of other diverse species (FIG. 3). This provides evidence that *Acanthamoeba* is likely to have a pentafunctional AROM polypeptide. A further round of genome walking gave a specific product that when sequenced extends from the EPSP synthase into a region that shares predicted homology to previously identified shikimate kinases, the third enzyme present in the classical pentafunctional AROM structure (FIG. 10).

Portions of Chorismate Synthase, DAHP Synthase, Tryptophan Synthase Beta Subunit and Anthranilate Synthase are Amplified from *A. castellanii* cDNA.

PCR gave portions of cDNA that encode partial sequences of chorismate synthase, DAHP synthase, tryptophan synthase beta subunit and anthranilate synthase from *A. castellanii* (FIGS. 4, 5, 6 and 7).

Portions of DAHP Synthase, DHQS and EPSP Synthase are Amplified from *A. polyphaga* gDNA.

PCR gave portions of gDNA that encode a partial sequence of DAHP synthase, and the DHQS domain and a partial EPSP synthase domain from *A. polyphaga* (FIGS. 8 and 9).

REFERENCES

Auran, J. D., M. B. Starr, and F. A. Jakobiec. 1987. *Acanthamoeba* keratitis. A review of the literature. Cornea. 6: 2-26.

Beattie, T. K., D. V. Seal, A. Tomlinson, A. K. McFadyen, and A. M. Grimason. 2003. Determination of amoebicidal activities of multipurpose contact lens solutions by using a most probable number enumeration technique. J. Clin. Microbiol. 41: 2992-3000.

Borazjani, R. N., L. L. May, J. A. Noble, S. V. Avery, and D. G. Ahearn. 2000. Flow cytometry for determination of the efficacy of contact lens disinfecting solutions against *Acanthamoeba* spp. Appl. Environ. Microbiol. 66: 1057-1061.

Buck, S. L., and R. A. Rosenthal. 1996. A quantitative method to evaluate neutralizer toxicity against *Acanthamoeba castellanii*. Appl. Environ. Microbiol. 62: 3521-3526.

Butler, J. R., Alworth, W. L., Nugent, M. J., 1974. Mechanism of dehydroquinase catalysed dehydration 1. Formation of a shiff base intermediate. J. Am. Chem Soc, 96, 1617-1618.

Coggins, J. R., K. Duncan, I. A. Anton, M. R. Boocock, S. Chaudhuri, J. M. Lambert, A. Lewendon, G. Millar, D. M. Mousdale, and D. D, Smith 1987. The anatomy of a multifunctional enzyme. Biochem. Soc. Trans. 15: 754-9.

Cohen, E. J., H. W. Buchanan, P. A. Laughrea, C. P. Adams, P. G. Galentine, G. S. Visvesvara, R. Folberg, J. J. Arentsen, and P. R. Laibson. 1985. Diagnosis and management of *Acanthamoeba* keratitis. Am. J. Ophthalmol. 100: 389-395.

Connor, C. G., S. L. Hopkins, and R. D. Salisbury. 1991. Effectivity of contact lens disinfection systems against *Acanthamoeba culbertsoni*. Optom. Vis. Sci. 68:138-141.

Culbertson, C. G., P. W. Ensminger, and W. M. Overton. 1966. *Hartmannella* (*Acanthamoeba*). Experimental chronic, granulomatous brain infections produced by new isolates of low virulence. J. Clin. Pathol. 46: 305-314.

Duncan, K., R. M. Edwards and J. R. Coggins 1987. The pentafunctional arom enzyme of *Saccharoinyces cerevisiae* is a mosaic of monofunctional domains. Biochem. J. 246, 375-86.

Hawkes, T. R., T. Lewis, J. R. Coggins., D. M. Mousdale, D. J. Lowe, R. N. Thorneley 1990. Chorismate synthase. Pre-steady-state kinetics of phosphate release from 5-enolpyruvylshikimate 3-phosphate. Biochem J. 265, 899-902

Hugo, E. R., W. R. McLaughlin, K. H. Oh, and O. H. Tuovinen. 1991. Quantitative enumeration of *Acanthamoeba* for evaluation of cyst inactivation in contact lens care solutions. Invest. Ophthalmol. Vis. Sci. 32: 655-657.

Khunkitti, W., S. V. Avery, D. Lloyd, J. R. Furr, and A. D. Russell. 1997. Effects of biocides on *Acanthamoeba castellanii* as measured by flow cytometry and plaque assay. J. Antimicrob. Chemother. 40: 227-233.

Kinyanjui S M, Mberu E K, Winstanley P A, Jacobus D P, Watkins W M. (1999) The antimalarial triazine WR99210 and the prodrug PS-15: folate reversal of in vitro activity against Plasmodium falciparum and a non-antifolate mode of action of the prodrug. Am J Trop Med Hyg. 60(6):943-7.

Marciano-Cabral F, R. Puffenbarger, and G. A. Cabral. 2000. The increasing importance of *Acanthamoeba* infections. J. Eukaryot. Microbiol. 47: 29-36.

McBride, J., Ingram, P. R., Henriquez, F. L. & Roberts, C. W. (2005). Development of a colorimetric microtitre plate assay for assessment of antimicrobials against *Acanthamoeba* (species). Journal of Clinical Microbiology 43, 629-634.

Moore, M. B., J. P. McCulley, M, Luckenbach, H, Gelender, C, Newton, M. B. McDonald, and G. S. Visvesvara. 1985. *Acanthamoeba* keratitis associated with soft contact lenses. Am. J. Ophthalmol. 100: 396-403.

Min, G. S., and J. R. Powell 1997. Long-distance genome walking using long and accurate polymerase chain reaction. Biotechniques 24: 398-400.

Mousdale, D. M., M. S. Campbell, and J. R. Coggins 1987. Purification and characterisation of a bifunctional dehydroquinase-shikimate: NADP oxidoreductase from peas seedlings. Phytochem. 26, 2665-2670.

Mousdale, D. M. and J. R. Coggins 1986. Rapid chromatographic purification of glyphosate-sensitive 5-enolpyruvylshikimate 3-phosphate synthase from higher plant chloroplasts. J. Chromatogr. 367, 217-222.

Nichols, B. P. and J. M. Green 1992. Cloning and sequencing of *Escherichia coli* ubiC and purification of chorismate lyase. J. Bacteriolo. 174, 5309-5316.

Roberts, F., C. W. Roberts, J. J. Johnson, D. Kyle, T. Krell, J. R. Coggins, G. H. Coombs, W. K. Milhous, S. Tzipori, D. J. P. Ferguson, D. Chakrabarti, & R. McLeod (1998). Evidence for the shikimate pathway in apicomplexan parasites. Nature 393: 801-805.

Roberts, C. W., F. Roberts, R. E. Lyons, M. Kirisits, E. Mui, J. Finnerty, D. J. P. Ferguson, J. R. Coggins, T. Krell, G. H. Coombs, W. Milhous, D. Kyle, S. Tzipori, J. Barnwell, J. B. Dame, J. Carlton, & R. McLeod (2002). The shikimate pathway and its branches in apicomplexan parasites. Journal of Infectious Diseases 185: S25-36.

Seal, D. V. 2003. *Acanthamoeba* keratitis update-incidence, molecular epidemiology and new drugs for treatment. Eye. 17: 893-905.

Seijo Martinez, M., G. Gonzalez-Mediero, P. Santiago, A. Rodriguez De Lope, J. Diz, C. Conde, and G. S. Visvesvara. 2000. Granulomatous amebic encephalitis in a patient with AIDS: isolation of acanthamoeba sp. Group II from brain tissue and successful treatment with sulfadiazine and fluconazole. J. Clin. Microbiol. 38: 3892-3895.

Sirichaiwat C, Intaraudom C, Kamchonwongpaisan S, Vanichtanankul J, Thebtaranonth Y, Yuthavong Y. (2204) Target guided synthesis of 5-benzyl-2,4-diamonopyrimidines: their antimalarial activities and binding affinities to wild type and mutant dihydrofolate reductases from Plasmodium falciparum. J Med Chem. 47(2):345-54.

Stehr-Green, J. K., T. M. Bailey, and G. S. Visvesvara. 1989. The epidemiology of *Acanthamoeba* keratitis in the United States. Am. J. Ophthalmol. 107: 331-336.

The invention claimed is:

1. A method of treating a subject suffering from a disease caused by a member of the Acanthamoebida family, said method comprising the step of:
   a) administering to a subject a therapeutically effective amount of a compound capable of inhibiting the shikimate pathway in the Acanthamoebida member, wherein said compound is glyphosate and said Acanthamoebida member possesses the shikimate pathway, wherein said effective amount is in a topical formulation comprising glyphosate in a concentration of at least about 22 μM, wherein said disease is keratitis.

2. The method according to claim 1 wherein said Acanthamoebida member is *Acanthamoeba castellanii* and/or *Acanthamoeba polyphaga*.

* * * * *

SEQUENCE LISTING

<160> NUMBER OF SEQ ID NOS: 9

<210> SEQ ID NO 1
<211> LENGTH: 1452
<212> TYPE: DNA

<213> ORGANISM: A. castellanii

<400> SEQUENCE: 1

```
atgcagaaga agggagggga tttcgttgtg gaggatgtgc cggtggagcg ggtggaggga      60
ggcaaggagc cgatcgttat cggcaacgag atcctgcgca agggctggat cgcgcgcgac     120
atccgcgagc gagtgcccaa ggcggtgaag ttcgtcatcg tcaccgactc gaacgtgttc     180
gggctctacg gtcagacctt catctcgacc ttcgagcagg tgctccacat caagcccttt     240
gtcaaagtgc tgccaccggg cgaggagacc aagagccggc aggtcaagga ggagatcgaa     300
gatttcatgc tcgccaaggc ttgcaatcgc gacacctgcg tggtcgccct gggtggtggt     360
gtcattggcg atctcgctgg attcgtggct gccacctacc tccgaggggt gccttttcgtg    420
caagtaccaa ccaccctcct ggccatggtg gactcttcga tcggcggcaa gactggactc     480
aacccgccag cgggcaagaa cctcgtgggc gcgttccacc accccaaggc agtctacatc     540
gatctgtcgc tcctcaaaac tcttccccag cgcgagttct gtaacggcct tgccgaggtc     600
atcaagtctg gagtgatcag ggaccccgag ctgttcgaat gctggagac caacgtggac     660
ggcatcctca caacaggga ggagcgtttg cttcgggaga tcgtgcaccg atcggccaag     720
atgaaggccg aggtggtcat gatggacgcc aacgaaaacg gcatccgttg catcctcaac     780
tacggacaca cgatcggcca tgccatcgag gcctttgcct tcccgctcct tctgcacgga     840
gagtgcgtgt cgattggcat ggtacgcgca cgacacacaa cgcacacgca cgcacacgcg     900
tcatttcagt taacacatcg gttttttcaat gtggcacggc ggtaccaggt gctcgagagc     960
aagctggcac agaagatgaa ccacctcaag aacctcaact tcattggccg gctgacgcga    1020
tgcctgcagg cctacaagct cgaagacctg atcaacaaga tgctcatcga caagaagaac    1080
gccaacagca acatccgatg cgtgatcgtc aaggacttcg gcgatgtgtt cgaacacccc    1140
gtcgttgttg acaaggacac gctcaggttt gtgcttttgc cctccgtggc ggtggagccc    1200
acccagagcg gcgtgagcgg cgtgatcacc gtgcccggct ccaagtcgat ctccaaccgc    1260
gtgttgactc ttgccgccct gggcgaagga ggcgaatgtc acatcaaggg gcttctctcg    1320
gccgacgaca cgggcgtgat gctcgccgcg cttcgacgac tcggtgtcca gtacaagtgg    1380
ctcgaccaag gcctcgtaag cgcctccccc ctgcatctgt ctgccgacaa cagctcaccc    1440
cagtcaccac cc                                                        1452
```

<210> SEQ ID NO 2
<211> LENGTH: 484
<212> TYPE: PRT
<213> ORGANISM: A. castellanii

<400> SEQUENCE: 2

```
Met Gln Lys Lys Gly Gly Asp Phe Val Val Glu Asp Val Pro Val Glu
1               5                   10                  15

Arg Val Glu Gly Gly Lys Glu Pro Ile Val Ile Gly Asn Glu Ile Leu
            20                  25                  30

Arg Lys Gly Trp Ile Ala Arg Asp Ile Arg Glu Arg Val Pro Lys Ala
        35                  40                  45

Val Lys Phe Val Ile Val Thr Asp Ser Asn Val Phe Gly Leu Tyr Gly
    50                  55                  60

Gln Thr Phe Ile Ser Thr Phe Glu Gln Val Leu His Ile Lys Pro Phe
65                  70                  75                  80

Val Lys Val Leu Pro Pro Gly Glu Glu Thr Lys Ser Arg Gln Val Lys
                85                  90                  95
```

```
Glu Glu Ile Glu Asp Phe Met Leu Ala Lys Ala Cys Asn Arg Asp Thr
            100                 105                 110

Cys Val Val Ala Leu Gly Gly Val Ile Gly Asp Leu Ala Gly Phe
        115                 120                 125

Val Ala Ala Thr Tyr Leu Arg Gly Val Pro Phe Val Gln Val Pro Thr
130                 135                 140

Thr Leu Leu Ala Met Val Asp Ser Ser Ile Gly Gly Lys Thr Gly Leu
145                 150                 155                 160

Asn Pro Pro Ala Gly Lys Asn Leu Val Gly Ala Phe His His Pro Lys
                165                 170                 175

Ala Val Tyr Ile Asp Leu Ser Leu Leu Lys Thr Leu Pro Gln Arg Glu
            180                 185                 190

Phe Cys Asn Gly Leu Ala Glu Val Ile Lys Ser Gly Val Ile Arg Asp
        195                 200                 205

Pro Glu Leu Phe Glu Leu Leu Glu Thr Asn Val Asp Gly Ile Leu Asn
    210                 215                 220

Asn Arg Glu Glu Arg Leu Leu Arg Glu Ile Val His Arg Ser Ala Lys
225                 230                 235                 240

Met Lys Ala Glu Val Val Met Met Asp Ala Asn Glu Asn Gly Ile Arg
                245                 250                 255

Cys Ile Leu Asn Tyr Gly His Thr Ile Gly His Ala Ile Glu Ala Phe
            260                 265                 270

Ala Phe Pro Leu Leu Leu His Gly Glu Cys Val Ser Ile Gly Met Val
        275                 280                 285

Arg Ala Arg His Thr Thr His Thr His Ala His Ala Ser Phe Gln Leu
    290                 295                 300

Thr His Arg Phe Phe Asn Val Ala Arg Arg Tyr Gln Val Leu Glu Ser
305                 310                 315                 320

Lys Leu Ala Gln Lys Met Asn His Leu Lys Asn Leu Asn Phe Ile Gly
                325                 330                 335

Arg Leu Thr Arg Cys Leu Gln Ala Tyr Lys Leu Glu Asp Leu Ile Asn
            340                 345                 350

Lys Met Leu Ile Asp Lys Lys Asn Ala Asn Ser Asn Ile Arg Cys Val
        355                 360                 365

Ile Val Lys Asp Phe Gly Asp Val Phe Glu His Pro Val Val Val Asp
    370                 375                 380

Lys Asp Thr Leu Arg Phe Val Leu Pro Ser Val Ala Val Glu Pro
385                 390                 395                 400

Thr Gln Ser Gly Val Ser Gly Val Ile Thr Val Pro Gly Ser Lys Ser
                405                 410                 415

Ile Ser Asn Arg Val Leu Thr Leu Ala Ala Leu Gly Glu Gly Gly Glu
            420                 425                 430

Cys His Ile Lys Gly Leu Leu Ser Ala Asp Asp Thr Gly Val Met Leu
        435                 440                 445

Ala Ala Leu Arg Arg Leu Gly Val Gln Tyr Lys Trp Leu Asp Gln Gly
    450                 455                 460

Leu Val Ser Ala Ser Pro Leu His Leu Ser Ala Asp Asn Ser Ser Pro
465                 470                 475                 480

Gln Ser Pro Pro

<210> SEQ ID NO 3
<211> LENGTH: 678
<212> TYPE: DNA
<213> ORGANISM: A. castellanii
```

<400> SEQUENCE: 3

```
atgagcagct tggcagagc gtttcgagtg accaccttcg gtgaatcgca cggcggcgga      60
gtgggatgca ttatctcctt tgcagatgga gtgccgccct gcctgcccct caccgaagcc    120
gacatccagc cgcagctcag ccgtcgccgc cccggccaga gctccctcac cacccccgtg    180
tctcatcaga ggaatgaggc ggaccaggtg aagatccagg ccggcacgga gaacgggtac    240
acgctgggct cgccgatcag cctcttcgtg gccaaccagg accagcggcc cgtcgactac    300
tcggacatgt ccaagattga ggcggcaaag gctgacaagg acagcatcgg cggcgtggtg    360
acgtgcgtgt gccgtaacgt accgacgggc ctgggcgagc cctgcttcga caagctcgag    420
gccatgctcg cccacgccat gctctccatc ccggccacga aggggttcga gatcggcagc    480
ggcttcgcgg gcacgcggat gcggggcagc aagcacaacg ccccttcgt ggtcaagacc     540
ggggccgacg gcaagaagcg gctcggtacc actaccaacc acagcggcgg catccagggc    600
ggaatcacca acggcgaaca cgtcgtcttc aaggtggcgt tcaagccgcc ggccacgatt    660
agccaggcgc agaagacg                                                  678
```

<210> SEQ ID NO 4
<211> LENGTH: 797
<212> TYPE: DNA
<213> ORGANISM: A. castellanii

<400> SEQUENCE: 4

```
gagttcttgg acaccatcag cccgcagttc gtggccgacc tggtctcctg gggcgccatc     60
ggagcgcgca ccaccgagag ccaggtgcac cgcgagctgg cctccggtct gtccgtccct    120
gtcggttca agaatggtag cgcgccctgcc ttgcctgtgc gattgtgtgg cgtgtgcgtg    180
tgcggtggtg ctaacaagat ggtacccgag ccaggcacgg atggtggagt gcaggtggcg    240
ctggatgcta tcaaggcggc gtcgaatccc catcagttcc tgggtgtgac gaagcagggc    300
ctcaccgcga tcgtgcgaac gcgaggcaac gacgcgtgcc acatcgtgct gcgcggcggc    360
aagggcggac ccaactatga cggggagagc gtacagaaga cggtcgagct ggcgcgcaag    420
gccaagctca gcacctcgat catgatcgac tgctcgcacg acaactcgcg caagaaccac    480
gccaaccagc ccatcgtctc cgccgccatc gtacgccaac cgcacgccca tcgtctcatc    540
tctttcatca tcaaacgctc acgcacaaca cgacacacac gacacacgac acacaggcgg    600
agcaggtggc ggctgggtgt gccgacatca tcggagtgat gattgagagc aacctcgtcg    660
agggccgaca ggaccctcccc gccgacggtc cgcagtacct gcagtacggg aagagcatca    720
ccgacgcgtg catcagcttc aaggacacga tccccgtgct cgagtccctc gccgcggccg    780
tgcgagaacg gaggaag                                                   797
```

<210> SEQ ID NO 5
<211> LENGTH: 366
<212> TYPE: DNA
<213> ORGANISM: A. castellanii

<400> SEQUENCE: 5

```
ggcacgttcc atccgttcat caacgacaag gaggtcaaga tcgtgggcgt gcaggcggcg     60
ggcgagggtg tccatacgga caagcactgc gcgacgctgg tcaagggcac gcccggcgtg    120
ctgcacggca cgcgcacgat gctgctgcag gaccccgagg ccagatcaa gtccacgcac    180
tcgatctcgg ccgggctgga ctaccccggc gtcggacccg agcacgcgtg gctgctcgag    240
tcgaagcgcg ccgagtacgt ggcggtgagc gacgagcagg ccctggaggg cttcaaggag    300
```

```
ctcacgcgca aggagggcct catgccggcc ctggagacgt cgcacgccgt ctaccacgcc    360
atccag                                                               366
```

<210> SEQ ID NO 6
<211> LENGTH: 325
<212> TYPE: DNA
<213> ORGANISM: A. castellanii

<400> SEQUENCE: 6

```
atccgagcgc tggcgggcaa gattccgatc ctgggcgtgt gtctgggcca cgagtgtatg     60
gtggaggagt acggcggcgt gatcgagcac tgcggcgaga tcgtgcacgg caagacctcc   120
aacatcattc acgacggcaa gggcctctac gtcggtacgc accccgttt agatttatat    180 aacaattatt ataatttgta tttatacatt taaaaatgca aacgctctcc gggcgacaga   240
cattcccaac aacgtgccgg tcatccggta tcattcgctg gcggcgaggc acccgccct    300 gccgccggac tttgttgtga cctcc                                          325
```

<210> SEQ ID NO 7
<211> LENGTH: 858
<212> TYPE: DNA
<213> ORGANISM: A. polyphaga

<400> SEQUENCE: 7

```
gagttcttgg acaccatcag cccgcagttc gtggccgacc tggtctcctg gggcgccatc     60
ggagcgcgca ccaccgagag ccaggtgcac cgcgagctag cctccggtct gtccgtccct   120
gtcggtttca agaacggtag gcgccctgcc ttgcgtgtgc gtgcgtgcgt gcgtgtgtgc   180
gtgtgtcctg tcatcatcgc ggatggtgcg ggtagtgagt cggttgtgtg cgtgtgcggt   240
ggtgcgtgtg cgtgtgcgtg tgcggtggtg ctaatgagat ggtcccggac caggcacgga   300
tggtggagtg caggtggcgc tggatgccat caaggcggcg tcgaatcccc atcagttcct   360
gggcgtgacg aagcagggcc tcaccgcgat cgtgcgaacg cgaggcaacg acgcgtgcca   420
catcgtgctg cgcggcggca agggcggacc caactatgac ggggagagcg tgcagaagac   480
ggtcgagctg gcgcgcaagg ccaagctcag cacctcgatc atgatcgact gctcgcacga   540
caactcgcgc aagaaccacg ccaaccggcc catcgtctcc gccgccatcg tacgcctacc   600
gcacgcccta tctctggcat catcccatgc tcacccacac acgcacacac tacacaggcg   660
gagcaggtgg cggctgggtg tgccgacatc atcggagtga tgatcgagag caacctcgtc   720
gagggccgac aggacctccc cgccgacggt ccgcagtacc tgcagtacgg caagagcatc   780
accgacgcgt gcatcagctt caaggacacg gtgcccgtgc tcgagtccct cgccgcggcc   840
gtgcgagaac ggaggaag                                                  858
```

<210> SEQ ID NO 8
<211> LENGTH: 768
<212> TYPE: DNA
<213> ORGANISM: A. polyphaga

<400> SEQUENCE: 8

```
gacgccaacg aaaacggcat ccgttgcatc ctcaactacg acacacgat cggtcacgcc      60 atcgaggcct ttgccttccc gctccttctg cacggagagt gcgtgtcgat ggcatggta    120 cacacgcacg acacacaaca cacgcacgca tgcacgcaca caccaccgca cgcacgacac   180
acgcgtcatt ttagttaaca cacgtggcac ggcggtacca ggtgctcgag agcaagctgg   240
cacagaagat gaaccacctc aagaacctca acttcattgg ccggctgacg cgatgtctgc   300
```

| | |
|---|---|
| aggcctacaa gctccccgtc gtggtcccca aaccgaagaa agtatgtgtg cgtgtgcgtg | 360 |
| tgcggtggtg cgtgtgcgtg cgtgcgatgc tggtgactca ccacgtccac taccaacagc | 420 |
| aacagggcgg cgatcagggc aagcgaaagg agggaacgct cgaattcacg ccggaagacc | 480 |
| tgatcaacaa gatgctcatc gacaagaaga acgccaacag caacatccga tgcgtgatcg | 540 |
| tcaaggactt cggcgatgtg ttcgaacacc ccgtcgtcgt cgacaaggac acgctcaggt | 600 |
| attcttctgc ccttgtgtgt gtgtgttgtg tgtgtgtgtg tgtggtgcgc ctgagagcta | 660 |
| agtgtgactg gaacaacagg tttgtgcttt tgccctctgt ggaggtggag cccacccaaa | 720 |
| gcggcgtgag cggcgtgatc accgtgcccg gctccaagtc gatctcca | 768 |

<210> SEQ ID NO 9
<211> LENGTH: 3282
<212> TYPE: DNA
<213> ORGANISM: A. castellanii

<400> SEQUENCE: 9

| | |
|---|---|
| atggacgcca acgaaaacgg catccgttgc atcctcaact acggacacac gatcggccat | 60 |
| gccatcgagg cctttgcctt cccgctcctt ctgcacggag agtgcgtgtc gattggcatg | 120 |
| gtacgcgcac gacacacaac gcacacgcac gcacacgcgt catttcagtt aacacatcgg | 180 |
| ttttcaatg tggcacggcg gtaccaggtg ctcgagagca agctggcaca gaagatgaac | 240 |
| cacctcaaga acctcaactt cattggccgg ctgacgcgat gcctgcaggc ctacaagctc | 300 |
| cccgtcgtgg tccccaaacc gaagaaagtg cgtgtgcatg tgtgtgcatg tgtgtgcatg | 360 |
| tgtgtgcggt gtgtgcggtg tgtgtggtgt gtgcggtgtg tgcgtgcgat gctggtgact | 420 |
| cacatccaca tccacgacca acagcaacag ggcggcgatc agggcaagcg aaaggaggga | 480 |
| acgctcgaat tcacgccgga agacctgatc aacaagatgc tcatcgacaa gaagaacgcc | 540 |
| aacagcaaca tccgatgcgt gatcgtcaag gacttcggcg atgtgttcga acaccccgtc | 600 |
| gttgttgaca aggacacgct caggtattct tctgcccttg tgtatgtgkt gtgtgtgtgt | 660 |
| gtgtgtgtgt cgagcgcgag tgtgtgtcgt gagcgtgtgt cgtgcgcgtg tgctctaatt | 720 |
| gcgactggac caacaggttt gtgcttttgc cctccgtggc ggtggagccc acccagagcg | 780 |
| gcgtgagcgg cgtgatcacc gtgcccggct ccaagtcgat ctccaaccgc gtgttgactc | 840 |
| ttgccgccct gggcgaaggt atgccactct ctcttccctc ctctcgccct tcagtacatc | 900 |
| caacaaacaa gtcaagtttg acgaacaaac accacgcgcg cgcgcgcgcg cacacacaca | 960 |
| cacacacaca cacacacaca cacacacaca ctctggcttg ctcgcttgca cacaggcgaa | 1020 |
| tgtcacatca aggggcttct ctcggccgac gacacgggcg tgatgctcgc cgcgcttcga | 1080 |
| cgactcggtt ccagtacaa gtggctcgac caaggcctcg taagcgcctc ccccctgcat | 1140 |
| ctgtctgccg acaacagctc accccaccca ccacccacca cccgccgccg ccagacgctg | 1200 |
| tacatcaagg gcagcggagg acagctgcag ccgccgaagg agcccgagrt cccattcttc | 1260 |
| ctgggcaacg ccrgcacggc gtcgcgcttc ctgaccacca tgtgcaccct cgtcaccccg | 1320 |
| ccggctggta ccaccatttc tcttgcttct cggccggttc cttggctccc cagtcgactg | 1380 |
| tcgactcatg tcgctaaccg ccggcacagg ctcgacggaa aaggtgtcga cgatcttgac | 1440 |
| gggggtcgac aggctcaagg ggcggcccat cagcgatctc gtggaggcgc tgcgggatga | 1500 |
| acggctgcgt catcaactac ctcgagaagg agggctactt ccccatcgaa gtggtgcgtg | 1560 |
| ccctgagcgc cgatgcgtgt gcggtggtgc gtgtgcgtgt gcgactgtgt gtgtcgacta | 1620 |
| gcgaccaaca accccgggc tggcgtcaac tcgctcgcag gtcggtggta aggggctgaa | 1680 |

```
cggtggtgtg atcaacctct cggccaagct tagcagccag tacgtgtcct ccatccttct    1740
ctcggccccg tacgcgctca acgacgtcga cctgcagatc aaaggtggcc acccgtctct    1800
tccttgcgtt gtgtcgtgta cgccgtgtgc gccgtgcgcc gtgtgcgtgt gcgtgtgcgc    1860
cgtgcgagta aactgaaagg gttctgcttt gtattggcag gtgaggccgt ttcgcagccg    1920
ttcatcgaga tgaccatcaa ggtgatgcag cagttcggcg tcaaggtcgt cgacacctcc    1980
aaggaggaca agatctcctg gttcatcccc cgcggcgttt accacaatcc caaggtaccc    2040
accatcacta gccgtcgtgt gtcgtgtgtc gtgggctgac ttctggtgtc gcgtgcggtc    2100
aggatttcgt cgtcgagccc gacgcgtcgt ytgcttcgta ccctctcgcg ctggcggcca    2160
tcaccggcgg cgagatcact gtggacaaca tcggctcgtc gagcgtgcag ggcgacgccc    2220
agttctacac ggtcatggag aagatgggct gcacagtcaa ccagaccacc acctccacca    2280
ccgtgaaggg tccggcgcgc ggtggcctga aggccgtcga catcgacatg tcatccatga    2340
ccgacacctt catgaccgtc gcagtcctcg ccgccgtcgc caccgtacgc acaggcccac    2400
cgcattcctt tcattccatt ccaggcactg tgcgagcatg cgccaagcaa tgttgacaat    2460
gtcgtcgaca cacacacaca cacaatacag ggcacgtcgc gtatttacaa catcgccaac    2520
cagcgcgtca aggagtgtaa tcgcattgcg gcgatggtga aagaactcgg gaagtgcggc    2580
gtgaccgctc gcgagctcga agacggtctg gagattgacg gttgcggcgg ggacatctcc    2640
aagctgcacg gcgccagcat cgaatgctac agggaccacc gaattgccat gaggtatgca    2700
cacgcaccat cgcacacgct ccacgtgcct gtgcttatcg tgtgtgtcgt gtgtgtgtgt    2760
cgtgtgtgtc gcgtgtgtgt cgcgtgtagc ttcggcgtgt tcggaacggt ggtgccgggc    2820
atcctgatca ccgacaagga gtgcgtcgac aagacctacc ccgacttctg gtacgacctc    2880
gagttccgct tcggcgtccg cctgtccgtg ccctctaccg agaacgagca gcaaaagccc    2940
gccgccgccg ccactgccga ggcgtcggtt gctgaccggc ccggaccgga cggcgacacc    3000
ggtcggtggt gctggtgggc atgcgcgggt caggcaagag cacgatgggc tcggccctcg    3060
ccgcgggcct gggctggaag ttcatcgaca tcgacgtcga gttcgaggcc tttgtgggcg    3120
agaagatccg gtccttcgtc gacgcgcacg gctggccggc cttccgggcc aaggaggagg    3180
agctcgtgcg ccaggtggtc gaggcccacc cgcagcggac cgtcatctcc accggcggag    3240
gcatcgtaat ctccccgacc gctttcgagt acctccattc cc                       3282
```